United States Patent
Vrouwe et al.

(10) Patent No.: US 9,315,768 B2
(45) Date of Patent: Apr. 19, 2016

(54) BIOLOGICAL MICROFLUIDICS CHIP AND RELATED METHODS

(75) Inventors: Elwin Xander Vrouwe, Enschede (NL);
Eric Marijn Wielhouwer, Leiden (NL);
Johannes Oonk, Enschede (NL);
Marinus Bernardus Olde Riekerink, Enschede (NL); Michael Keith Richardson, Leiden (NL)

(73) Assignee: Universiteit Leiden, Leiden (NL)

( * ) Notice: Subject to any disclaimer, the term of this patent is extended or adjusted under 35 U.S.C. 154(b) by 101 days.

(21) Appl. No.: 13/378,924

(22) PCT Filed: Jun. 15, 2010

(86) PCT No.: PCT/EP2010/003579
§ 371 (c)(1),
(2), (4) Date: Mar. 15, 2012

(87) PCT Pub. No.: WO2010/149292
PCT Pub. Date: Dec. 29, 2010

(65) Prior Publication Data
US 2012/0164679 A1    Jun. 28, 2012

(30) Foreign Application Priority Data
Jun. 16, 2009 (GB) .................................. 0910330.0

(51) Int. Cl.
*C12M 1/34* (2006.01)
*C12M 3/00* (2006.01)
(Continued)

(52) U.S. Cl.
CPC .............. *C12M 23/12* (2013.01); *B01L 3/5027* (2013.01); *C12M 23/16* (2013.01);
(Continued)

(58) Field of Classification Search
CPC .................. G01N 33/54366; G01N 33/54373; B01J 2219/00722; B01J 19/0046; B82Y 30/00
USPC .................................................. 435/29, 287.1
See application file for complete search history.

(56) References Cited

U.S. PATENT DOCUMENTS 6,488,892 B1    12/2002    Burton et al.
7,033,840 B1 *   4/2006    Tagge et al. ................... 436/147

FOREIGN PATENT DOCUMENTS

EP          488769 A2     4/1998
WO      2005023124 A2     3/2005
(Continued)

OTHER PUBLICATIONS

International Search Report; PCT/EP2010/003579 dated Sep. 30, 2010.

*Primary Examiner* — Michael Hobbs
(74) *Attorney, Agent, or Firm* — TraskBritt, P.C.

(57) ABSTRACT

A biological microfluidics chip comprising a substrate, a microfluidic inlet port defining an opening in a surface of the substrate, and a microfluidic outlet port defining an opening in a surface of the substrate. The biological microfluidics chip also comprises a plurality of wells extending from a top surface of the substrate, wherein each well is bounded by one or more walls, and an inlet opening and an outlet opening are provided in a wall of each of the plurality of wells. An inlet microfluidic channel is provided in the substrate to connect the microfluidic inlet port to each of the inlet openings in the walls of the wells, and an outlet microfluidic channel is provided in the substrate to connect each of the outlet openings in the walls of the wells to the microfluidic outlet port.

20 Claims, 7 Drawing Sheets

(51) Int. Cl.
  *C12M 1/32* (2006.01)
  *B01L 3/00* (2006.01)
  *C12M 3/06* (2006.01)
  *C12M 1/02* (2006.01)

(52) U.S. Cl.
  CPC ........... *C12M 41/18* (2013.01); *B01L 3/50851* (2013.01); *B01L 3/50853* (2013.01); *B01L 2300/0829* (2013.01); *B01L 2300/0877* (2013.01); *B01L 2300/185* (2013.01)

(56) References Cited

FOREIGN PATENT DOCUMENTS

| | | |
|---|---|---|
| WO | 2005059088 A1 | 6/2005 |
| WO | 2006097749 A1 | 9/2006 |
| WO | 2008035074 A2 | 3/2008 |
| WO | 2008072968 A2 | 6/2008 |
| WO | 2010023497 A1 | 3/2010 |
| WO | 2010149292 A1 | 12/2010 |

\* cited by examiner

BIOLOGICAL MICROFLUIDICS CHIP AND RELATED METHODS

CROSS-REFERENCE TO RELATED APPLICATION(S)

This is a national phase entry under 35 U.S.C. §371 of International Patent Application PCT/EP2010/003579, filed Jun. 15, 2010, published in English as International Patent Publication WO 2010/149292 A1 on Dec. 29, 2010, which claims the benefit under Article 8 of the Patent Cooperation Treaty to Great Britain Patent Application Serial No. 0910330.0, filed Jun. 16, 2009.

TECHNICAL FIELD

This disclosure relates to a biological microfluidics chip, and methods of using such a biological microfluidics chip. For convenience, a biological microfluidic chip may be referred to as a "biochip."

BACKGROUND

In biological and biomedical scientific research, it is commonplace to employ cultivation receptacles in which researchers cultivate cell cultures or embryos intended for study. One very common form of cultivation receptacle is a so-called microtiter plate that typically contains straight-sided cylindrical wells formed in a plate, the latter being of standardized shape and dimensions for locking retention in an analytical apparatus or robotic handler.

In practice, a microtiter plate typically includes an array of microtiter wells set in a grid-like pattern. One well-known arrangement includes 96 microtiter wells defining an array of eight rows containing twelve microtiter wells each. The design of the 96-well plate has become an industry standard format, specified by the Society for Biomolecular Screening.

A microtiter plate is typically manufactured from a transparent polymer such as acrylonitrile-butadiene-styrene ("ABS"). The transparency permits researchers to perform various optical tests on cells, embryos or larvae cultivated in the microtiter wells. In addition, microtiter wells are suitable for carrying out numerous tests and investigations that do not involve cell material.

The microtiter wells are open-ended at their in-use upper ends. Electronically controlled dosing apparatuses may be employed to inject each of the wells of a microtiter plate with a culture solution and, e.g., reagents, enzymes or other additives, the effect of which on cells in the microtiter wells it is desired to study.

As used herein, terms such as "upper," "above," "lower," "vertical," "horizontal," "upwardly," and "downwardly," for convenience, are construed with reference to a microtiter well or biological microfluidics chip in its operating orientation, as would arise when a biochip is placed flat on a horizontal surface such as a laboratory bench and the opening of the well is directed upward. It is, however, recognized that in use of a biochip or other cell cultivation receptacle, its orientation may change, e.g., as a result of being centrifuged or otherwise agitated, or by reason of being tilted or inverted as part of an experimental or observational procedure. The terms mentioned, and related terms, are not to be construed as limiting the scope of this disclosure to any particular orientation of the cultivation receptacles, or to any particular mode of use.

The paper entitled "Microfluidic System for On-Chip High-Throughput Whole-Animal Sorting and Screening at Subcellular Resolution" by Christopher B. Rohde, et al., published in *PNAS*, Aug. 28, 2007, vol. 104, no. 35, 13891-13895, discloses microfluidic devices consisting of flow and control layers made from flexible polymers. The flow layers contain microchannels for manipulating *C. elegans*, immobilizing them for imaging, and delivering media and reagents. The flow layers also contain microchambers for incubating the animals. The control layers consist of microchannels that, when pressurized, flex a membrane into the flow channels, blocking or redirecting the flow. Animals in the flow lines can be imaged through a transparent glass substrate using high-resolution microscopy.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

DISCLOSURE

According to first aspect of this disclosure, there is provided a biological microfluidics chip comprising:
a substrate;
a microfluidic inlet port defining an opening in a surface of the substrate;
a microfluidic outlet port defining an opening in a surface of the substrate; and
a plurality of wells extending from a top surface of the substrate, wherein each well is bounded by one or more walls, and an inlet opening and an outlet opening are provided in a wall of each of the plurality of wells;
one or more microfluidic inlet channels in the substrate that connect the microfluidic inlet port to each of the inlet openings in the walls of the wells; and
one or more microfluidic outlet channels in the substrate that connect the outlet openings in the walls of the wells to the microfluidic outlet port.

In conventional use, the inlet channel will convey fluid toward the well, and the outlet channel will convey fluid away from the well. However, it is possible to reverse this flow if required The biological microfluidics chip (biochip) can be used for the culture and study of cells, embryos and larvae located in the wells, and the microfluidic channels can be used to provide the wells with one or more microfluids, and also to remove one or more microfluids from the wells. In one example, drugs or other compounds and/or nutrients can be provided into a well for use in an experiment. In some embodiments, biological waste, metabolites and/or bacteria that would otherwise influence experiments performed in the wells can be removed from the wells through a microfluidics outlet channel.

Biochips, according to embodiments of this disclosure, can enable improved scientific experiments to be performed in the wells of the biochip, and more accurate and reliable results to be achieved at lower cost and higher speed.

The walls of the plurality of wells may comprise lateral boundaries, which may be considered as side walls, and may also comprise a bottom wall that may be considered as a floor of the well. The walls may be flat/planar or curved.

It will be appreciated that the term "microfluidics" is associated with the behavior, precise control and manipulation of fluids that are geometrically constrained to a small, typically sub-millimeter, scale.

The length of a microfluidic channel between the microfluidic inlet port and an inlet opening in a wall of a well may be substantially the same for each well, or a subset of wells. That is, although some of the wells may be further from the inlet port, the channel length between the inlet port and the opening for each well can be substantially the same.

In this way, the pressure, and hence the flow-rate, of fluids that are provided to the wells by a microfluidic channel, may be substantially the same for each of the individual wells. This can reduce the chances of cross-contamination of the contents of different wells and ensure that the same environmental conditions can be provided for each of the wells. One or more biological microfluidics chips disclosed herein can enable reliable, reproducible experiments to be performed in a plurality of different wells at the same time under the same conditions.

Similarly, the length of the microfluidic channels between each of the outlet openings in the walls of the wells and the microfluidic outlet port may be substantially the same for each well. In the same way as described above, this can ensure that fluids are removed from the wells at the same flow-rate for each well.

In some examples, the microfluidic channels may be of variable length so that the wells furthest from the port receive fluid at the same time, and under the same flow rate, as the wells nearest the inlet port. In each case, the same variable length can be applied to the corresponding microfluidic channel and each of the inlet/outlet openings in a well.

The biological microfluidics chip may further comprise:
a temperature control inlet port and a temperature control outlet port, and
a temperature control channel configured to transport temperature control fluid from the temperature control inlet port to the temperature control outlet port along a path that is in proximity to one or more of the plurality of wells such that, in use, heat is exchangeable between the temperature control liquid and the contents of the wells.

Providing such a built-in temperature control system can enable the biochip to be moved during an experiment, and the biochip is not restricted to a specific location because of a separate temperature control device.

Heat may be exchangeable in order to either heat or cool the contents of the well in use, and this may provide a stable and constant temperature among all wells.

The temperature control liquid may be an aqueous medium, an oil, or any other fluid that is suitable for maintaining a desired temperature as it travels along the temperature control channel.

One or more of the temperature control inlet port, temperature control outlet port and temperature control channels may be provided for a subset of the plurality of wells, and this can enable the temperature of individual wells, or subsets of wells, to be independently controlled.

In some examples, a single temperature control outlet port may be shared by wells that are associated with different temperature control inlet ports and/or temperature control channels. The temperature control channels from a plurality of inlet ports may join before opening at the outlet port such that the temperature control fluids, which have already served their purpose of heating or cooling the wells, of each individual channel are mixed together. This may be advantageous as it reduces the number of ports that are required for a biochip, and may be considered acceptable because the temperature control fluids from each temperature control inlet port will have served its purpose before they are mixed together for exiting the biochip.

The plurality of wells may comprise an array of wells. A separate temperature control inlet port and temperature control channel may be provided for each row of the array of wells. In this way, the temperature of the contents of rows of wells can be controlled independently of the temperature of wells in other rows.

The location of the inlet opening in a wall of a well may be lower than the outlet opening. This can enable microfluids that pass through the microfluidic channels into, and out of, the wells to be efficiently used in the wells. For example, having the first opening (inlet) lower than the second opening (outlet) can maintain a desired depth of fluid in the well, and can also ensure that the microfluids are efficiently passed through the wells.

The biological microchip may further comprise a second microfluidic inlet port and a second inlet opening in a wall of each of the wells. The second inlet opening may be in fluid communication with the second microfluidic inlet port by a second microfluidic inlet channel. In this way, more sophisticated experiments can be performed in the wells, for example, by combining different fluids from the different inlet ports in the wells. In one embodiment, different compounds may be provided to the same well via different inlet openings, for example, on different sides of the wells. It may also be possible to develop in a well a gradient effect between different fluids/compounds received from the first and second microfluid inlet ports.

The location of the second inlet openings in the wall of the wells may be lower than the outlet opening in the wall of the wells. This can ensure that fluids received at the first and second inlet openings can be effectively flushed through the well to the outlet opening.

It will be appreciated that biological microfluidics chips, according to embodiments of this disclosure, can have wells with multiple inlet and/or outlet openings and multiple inlet and/or outlet ports. It will also be appreciated that in some embodiments, an inlet port and inlet opening can be used as an outlet port and outlet opening, and vice versa.

In cases where there are more than one inlet opening and more than one outlet opening, an advantage is that if one opening becomes blocked, fluid can still flow in that well through the other openings.

The biological microfluidics chip may further comprise a lid that acts to seal the well. The lid may be sliding, self-sealing, removable, and/or heated. It may consist of a plastic, rubber, silicone or other such polymer film, bonded to the glass with heat or adhesives. Such lids may also be bonded to the chip by vacuum applied through dedicated microchannels in the chip. Such lids can be used to control the pressure in the wells, protect the upper openings of the wells from foreign bodies and fluid loss by evaporation, and/or uncover the upper openings of the wells when it is desired to insert something (for example, a product, a cell or group of cells, a further microfluid) into a well. A heated lid can reduce the likelihood of condensation forming on the lid, which can enable more accurate imaging operations to be performed through the lid.

The biological microfluidics chip may be located in a holder.

When the lid is in place, each well is sealed from the other wells. Therefore, there is no risk of cross-contamination (e.g., bacteria or other pathogens, drugs and other compounds) from one well to another via the upper opening of the well. The risk of cross-contamination between two or more wells via the microfluidics channels is reduced/prevented because the channels are relatively long and contain moving fluid. Therefore, contaminants would have to travel against the fluid flow to pass from one well to another.

It will be appreciated that a lid is not an essential feature of biological microfluidics chips according to embodiments of this disclosure, and that examples described herein can operate both in an open mode (that is without a lid in place) or a closed mode (that is, with a lid covering the upper openings in the wells).

The biological microfluidics chip may be reusable, for example, for a number of the same or different experiments. In some examples, it may be possible to clean the biochip after use by flushing cleaning fluids through the microfluidic channels and the wells. Cleaning the biochip may be an automated, or semi-automated, process that can clean the biochip to a reproducible standard. The chip can also be sterilized with fluids, irradiation or ultraviolet light. This can provide a more economical biochip, as biochips according to embodiments of the disclosure may need to be replaced less frequently than prior art biochips.

The substrate may be manufactured, at least in part, out of D263 glass. This type of glass has been found to reduce autofluorescence compared to known polystyrene products, and may be used in at least parts of the biochip through which imaging operations will be performed.

The plurality of wells may have a shape in vertical cross-section comprising two frustoconical shapes end to end, wherein the narrower ends of the frustoconical shapes are collocated. The wells may have an "hourglass" shape with a circular or square horizontal cross-section. The frustoconical shapes may be truncated cones or pyramids, for example, square-based pyramids.

The substrate of the biochip may comprise a top and a bottom layer, and the two frustoconical shapes may be collocated at the boundary between the top and bottom layer. Also, the first and/or second microfluidic channels may be provided between the top and bottom layer of the substrate. These features can provide convenient manufacture of the biochip.

One or more of the microfluidic channels may comprise a microfluidic valve. The microfluidic valves can be used to control the flow of fluids to and from the wells in accordance with the requirements of an experiment to be performed in the wells. For example, fluids can be delivered to the wells at desired times and in desired amounts in accordance with a particular experiment. The microfluidic valves may also be used to reduce the chances of cross-contamination between the contents of different wells.

According to a further aspect of this disclosure, there is provided a method of using a biological microfluidics chip, the biological microfluidics chip comprising:
  a plurality of wells;
  a microfluidic inlet port; and
  a microfluidic outlet port; the method comprising:
    providing cells to one or more of the plurality of wells, wherein the cells are for use in an experiment;
    providing a fluid to the microfluidic inlet port such that the fluid enters the one or more wells;
    removing a microfluid from the one or more wells via the microfluidic outlet port; and
    imaging the contents of the one or more wells in order to obtain results of the experiment in the one or more wells.

Examples of an experiment can include:

Experiments on zebrafish embryos/larvae, for example, for the development of the embryos/larvae over a period of days. Other embryos used can include those of other animals and plants.

In other embodiments, experiments can be performed on a monolayer of cells, for example, heart stem cells.

Tissues and cells can be grown on matrices or membranes placed inside the wells to allow cell and/or tissue growth in two or three dimensions.

The method may further comprise providing a temperature control fluid to a temperature control inlet port of the biological microchip in order to control the temperature of the contents of the one or more wells.

Providing cells to the one or more of the plurality of wells may comprise injecting the cells into an upper opening of the one or more wells, or introducing the cells via the microfluidics channels and ports.

BRIEF DESCRIPTION OF THE DRAWINGS

There now follows a description of preferred embodiments of the disclosure described herein, by way of non-limiting example, with reference to the accompanying drawings in which.

DETAILED DESCRIPTION

One or more embodiments described herein relate to a biological microfluidics chip having a plurality of wells/recesses, wherein each of the wells is in fluid communication with an inlet microfluidic channel and an outlet microfluidic channel. In this way, a fluid can be pumped through the wells in order to remove any bacteria or biological waste that may accumulate over time. Also, drugs or nutrients can be pumped into the wells via the microfluidic channels for use in the culture and study of embryos, larvae and adults of multicellular organisms, single/complex layered tissues/organs, cells or cell lines. Alternatively, or additionally, drugs or other compounds can be introduced into each well through an upper opening of the well.

In some embodiments, the microfluidic inlet channel between a microfluidic inlet port and an opening into a well may be of substantially the same length for each well, or a subset of wells. This can equalize pressure and retain flow rates between wells, to each well, or a subset of wells. In some examples, this can provide advantages as there is a reduced likelihood of cross-contamination between the contents of the separate wells. Each of the wells can be provided with clean fluid.

In other embodiments, the lengths of the microfluidic channels may be of varying lengths in order to equalize pressure and retain flow rates between an inlet port and one or more wells. It will be appreciated that the physical characteristics of the microfluidic inlet channel and microfluidic inlet port can be designed in any way that enables fluid to be provided to a plurality of wells at the same pressure with the same flow rate. Examples of the physical characteristics of the microfluidic inlet channel and/or microfluidic inlet port can include length, diameter, cross-sectional shape and surface characteristics that can affect fluid flow.

In some embodiments, the microfluidic outlet channel and microfluidic outlet port can be provided in a similar way to the microfluidic inlet channel and microfluidic inlet port in order to remove fluid from one or more of the wells.

Figure 1:
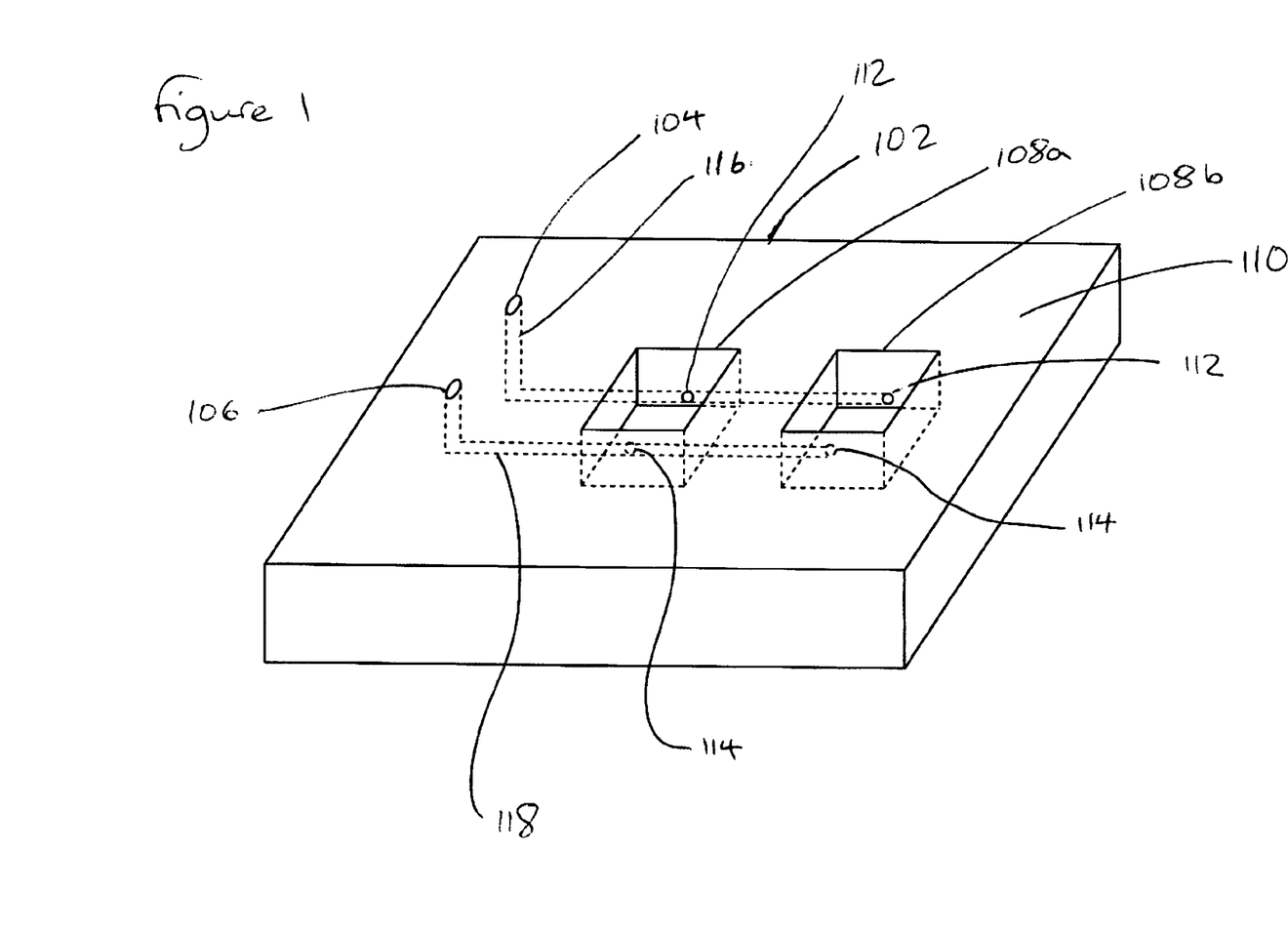
FIG. 1 illustrates a biological microfluidics chip according to an embodiment of this disclosure.

FIG. 1 illustrates a biological microfluidics chip (biochip) 100 according to an embodiment of this disclosure.

The biochip 100 comprises a substrate 102 having a microfluidic inlet port 104 and a microfluidic outlet port 106 defining openings in the top surface 110 of the substrate 102. The microfluidic inlet port 104 and microfluidic outlet port 106 may be considered as entrances of the microfluidic channels to an external environment. A plurality of recesses/wells 108 extend downwardly from the top surface 110 of the substrate 102.

In the embodiment shown in FIG. 1, only two wells 108a, 108b are illustrated in order to clearly be able to show the features of the wells 108. It will be appreciated that in practice, a biochip 100 may comprise 32 wells, 96 wells, 869 wells, or any number of wells that are required. An advantage of embodiments of the biochip 100 is that a large number of wells, and their associated microfluidic channels, can be provided in a small area. For example, a biochip according to an embodiment of the disclosure can accommodate 869 wells in the same area that a conventional microtiter plate would accommodate 96 wells.

Each of the wells 108 has a first opening 112 into a side wall of the well 108 and a second opening 114 into the opposite side wall of the well 108. The first opening 112 is an example of an inlet opening, and the second opening 114 is an example of an outlet opening. In this example, the wells 108 have a square horizontal cross-section. In other embodiments, wells 108 having cross-sections of any shape can be used, and the side walls may take any configuration of lateral boundaries, and may be flat/planar or curved, for example.

An inlet microfluidic channel/conduit 116 connects the microfluidic inlet port 104 to each of the inlet openings 112 in the wells 108. Similarly, an outlet microfluidic channel 118 connects the microfluidic outlet port 106 to each of the outlet openings 114 in the side walls of the wells 108.

In this example, the outlet openings 114 in the side walls of the wells 108 are higher (that is, closer to the upper surface from which the wells 108 extend) than the first openings 112. This configuration of inlet and outlet openings 112, 114 can be advantageous for causing a liquid that enters the well 108 from the inlet opening 112 to subsequently exit the well 108 through the outlet opening 114 without stagnating in the well 108. The configuration of openings 112, 114 can provide for an efficient and economical throughput of fluid through the well 108.

Figure 2:
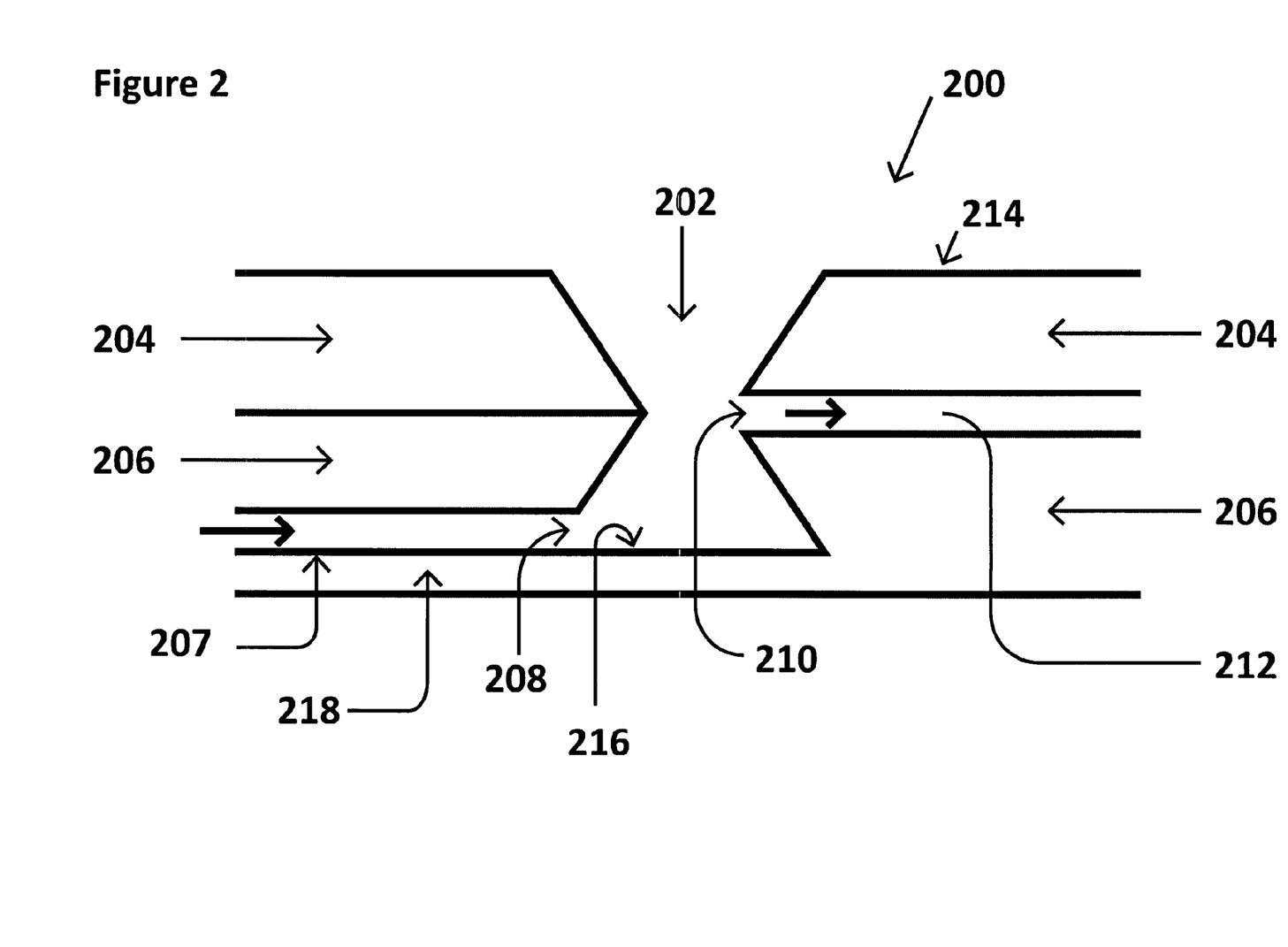
FIG. 2 illustrates a vertical cross-sectional view of a well of a biological microfluidics chip according to an embodiment of this disclosure.

FIG. 2 illustrates a cross-sectional side view through a well 202 of a biochip 200 according to an embodiment of this disclosure.

The biochip 200 comprises a first/top layer 204 of the substrate, a second/middle layer 206 of the substrate, and a third/bottom layer 218 of the substrate. Constructing the substrate as three layers can enable the microfluidic channels to be conveniently located within the body of the substrate, between the layers, as will be appreciated from the description below.

The well 202 in this example has a circular horizontal cross-section when viewed from above, although the structure illustrated in FIG. 2 is equally applicable to wells 202 having different cross-sectional shapes. The well 202 illustrated in FIG. 2 may be considered to have an "hourglass" shape in vertical cross-section.

The upper portion of the well 202 (that is, the portion of the well 202 that passes through the top layer 204) extends downwardly from the upper surface 214 of the first layer 204 of the substrate. The upper portion of the well 202 is, in this example, frustoconical in shape such that a cone associated with the upper portion of the well is pointing downward (away from the upper surface 214 of the first layer 204 of the substrate).

The well 202 has a bottom portion that extends into the second layer 206 of the substrate. Again, the horizontal cross-section of the lower portion of the well 202 is circular. In this example, the shape of the bottom portion of the well 202 is also frustoconical, but this time a cone associated with the frustoconical shape of the bottom portion of the well 202 points upward (toward the upper surface 214 of the first layer 204 of the substrate).

The horizontal cross-section of the well 202 at the boundary between the first layer 204 and second layer 206 of the substrate is substantially the same in each of the two layers 204, 206, such that a continuous well 202 is provided. It will be appreciated that the two point-to-point frustoconical parts of the well 202 can be seen to provide an "hourglass" shape in vertical cross-section when the well 202 is considered as a whole.

Providing a well 202 having an hourglass shape can be advantageous in terms of imaging the contents of the well 202. For example, a well 202 having this shape can enable the contents of the well 202 to be viewed/analyzed/measured from either the top or bottom of the biochip 200 without having to look through unnecessary layers 204, 206 of the substrate. The imaging may typically be performed by a microscope and the microfluidics chip may be made out of glass layers that are graded for microscopy. The boundary between the first, second and third layers 204, 206, 218 may not influence the imaging of the contents of the wells. In other embodiments, the well walls may be flat/planar such that the wells have a constant cross-sectional shape and size along their length.

The well 202 has a first opening 208 that is in fluid communication with a microfluidic channel 207. In this example, the microfluidic channel 207 is an inlet for a fluid. The first opening 208 is adjacent to a lower surface 216 of the well 202.

In addition, a second opening 210 is provided in the side wall of the well 202 between the first and second layers 204, 206 of the substrate. The second opening 210 is in fluid communication with a second microfluidic channel 212, which, in this example, is a microfluidic outlet channel. In use, an embryo or larvae, such as a zebra fish embryo or larva, can be located in the well 202, and nutrients, drugs or other compounds, can be pumped into the well 202 from the microfluidic inlet channel 207 and the first opening 208. Alternatively, these substances can be introduced via pipetting through the upper opening of the well.

One or more fluids can be removed from the well 202 through the second opening 210 in the side wall of the well 202, which opens into the microfluidic outlet channel 212. It will be appreciated that fluids that are extracted from the well 202 can include any waste products that may be formed in the well 202 over time, and can include products generated by the embryo/larvae and any bacteria or other pathogens, or biological waste, or drugs or other compounds, or shed tissues or substrates.

Figure 3:
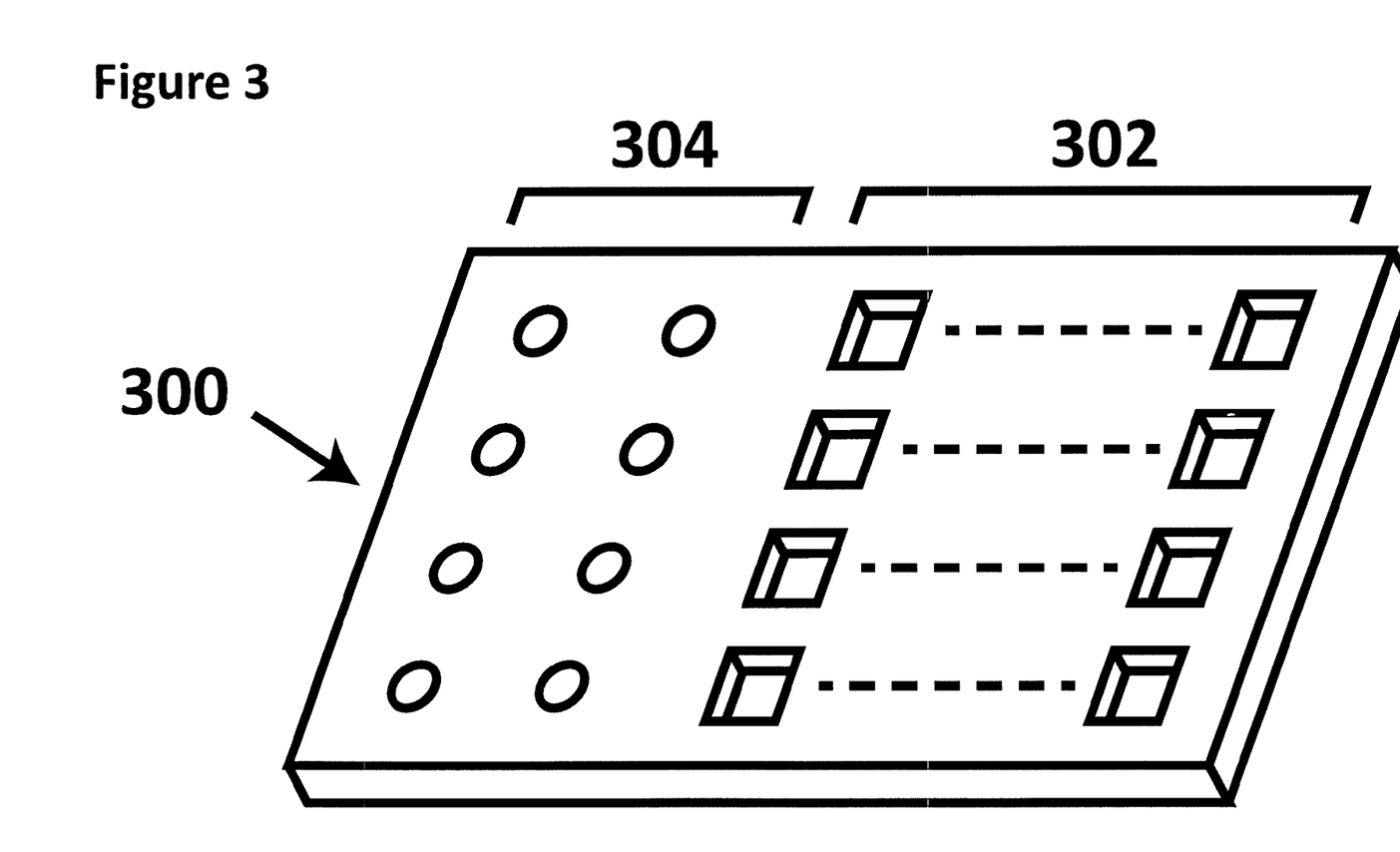
FIG. 3 illustrates a biological microfluidics chip according to another embodiment of the disclosure.

FIG. 3 illustrates a further embodiment of a biochip according to an embodiment of this disclosure.

The biochip 300 of FIG. 3 has an array of wells/recesses 302, which in this embodiment is a 4×8 array of 32 wells. In addition, eight inlet/outlet ports 304 are provided as a 4×2 array at one end of the biochip 300. It will be appreciated that other configurations of ports and wells are possible. The microfluidic channels extending from the inlet/outlet ports 304 are not shown in FIG. 3 to aid clarity. The fluidic channels extending from the inlet/outlet ports 304, and their interaction with the wells 302, are shown in more detail in FIGS. 4 and 5. It will be appreciated that the microfluidic channels illustrated in FIG. 4 and FIG. 5 separately, are in fact all present in the same biochip 300 illustrated in FIG. 3, but are illustrated separately for clarity. In this example, the wells are square in cross-section, when viewed from above, but other shapes are possible.

Figure 4:
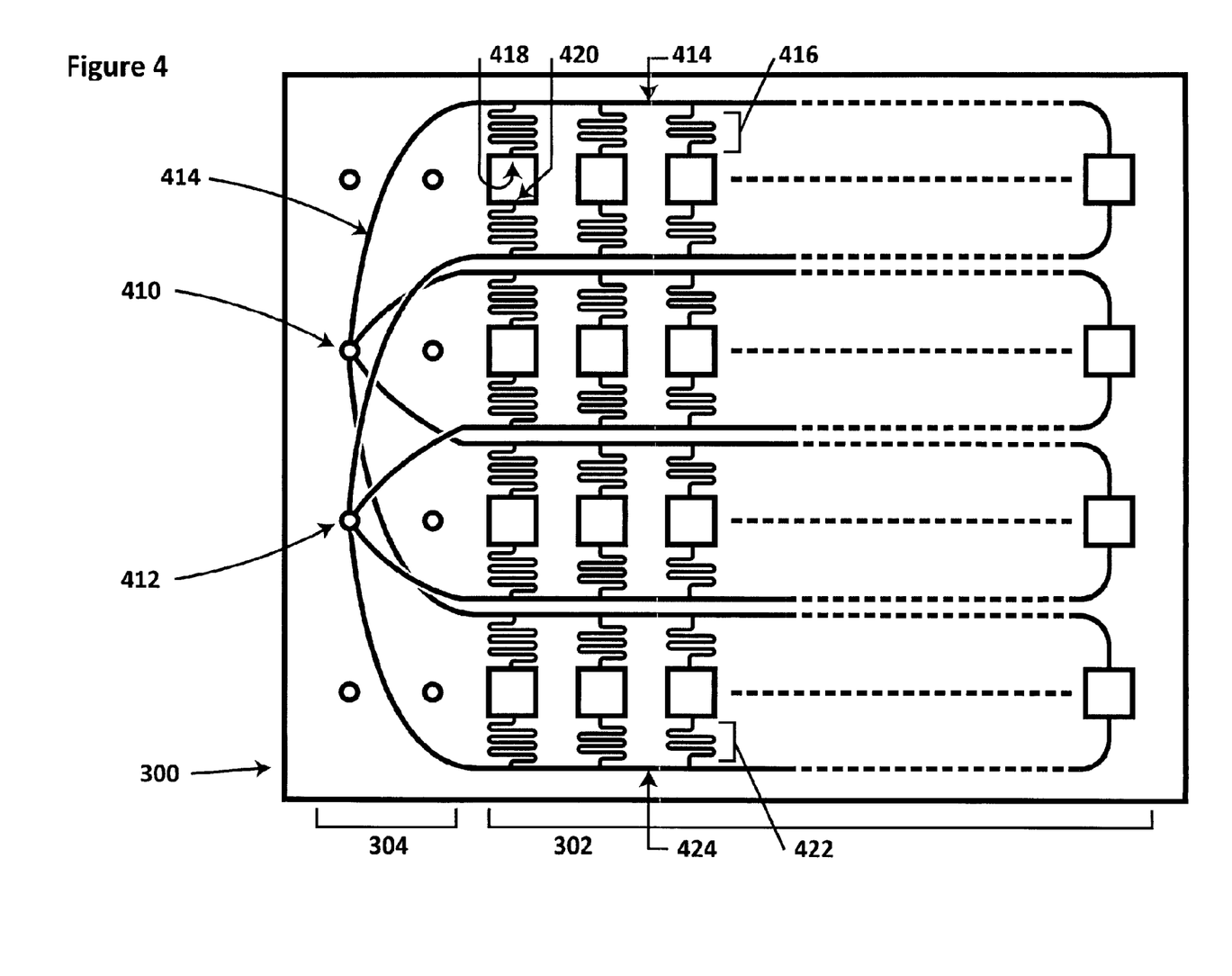
FIG. 4 illustrates further detail of the biological microfluidics chip of FIG. 3.

FIG. 4 shows the biochip 300 of FIG. 3, and the associated microfluidic inlet channels extending from a microfluidic inlet port 410 to the wells 302, and the microfluidic outlet channels (e.g., FIG. 6, 612) extending from a microfluidic outlet port 412 to the wells 302.

It will be appreciated that the microfluidic inlet port 410 is suitable for connecting to any microfluidic source, such as a source of drugs or nutrient medium that are to be provided to the wells 302. As illustrated in FIG. 4, microfluidic channels 414 extend in parallel from the microfluidic inlet port 410 to each row of wells 302. In this example, the wells are provided as a 4×8 array, and, therefore, four microfluidic channel branches 414 (one for each row) extend from the inlet port 410.

Each of the microfluidic channels 414 for a given row of wells 302 further branches off to be in fluid communication with a first opening 418 of each of the wells 302. Again, by branching off in this way, the microfluidic channels 414 may be seen to provide the fluid to each of the wells 302 in parallel.

In this example, the microfluidic channel 414 does not extend directly from the inlet port 410 to each of the first openings 418 in the wells 302, but is configured such that the channel length between the microfluidic inlet port 410 and each of the first openings 418 are of substantially the same length for each well to retain similar fluid flow rates for each well. This is achieved by providing a different channel length between a main artery of the microfluidic channel 414 and the first openings 418 in the different wells 302. For example, the microfluidic channel 414 may follow a path that doubles back on itself a number of times in order to provide an overall required channel length between the inlet port 410 and the first openings 418. This is shown in FIG. 4 as reference 416. It will be appreciated that the path length between a main artery of the microfluidic channel 414 and the first opening 418 should be shorter for wells 302 that are further from the inlet port 410 in order to provide an overall channel length between the inlet port 410 and the first openings 418 that provides substantially consistent fluid flow for each well. This can mean that resistance that is experienced when supplying a fluid to each well is substantially the same, regardless of the distance of the well from the port, and, therefore, the fluid is supplied evenly to each of the wells.

Providing microfluidic channels 414, 416 in this way can enable the physical characteristics experienced by the fluid when it is en route to a well 302 to be the same for each of the wells 302. This can provide a consistent pressure of fluid to each well 302, thereby providing a consistent flow rate and, therefore, can reduce the chances of the contents of the well 302 being forced back into the microfluidic inlet channel 414, 416. In turn, this can reduce the chance of cross-contamination between the contents of the individual wells 302.

The same structure is applied to the microfluidic output channel 424, 422 that connects the microfluidic outlet port 412 to second openings 420 in the wells 302.

Figure 5:
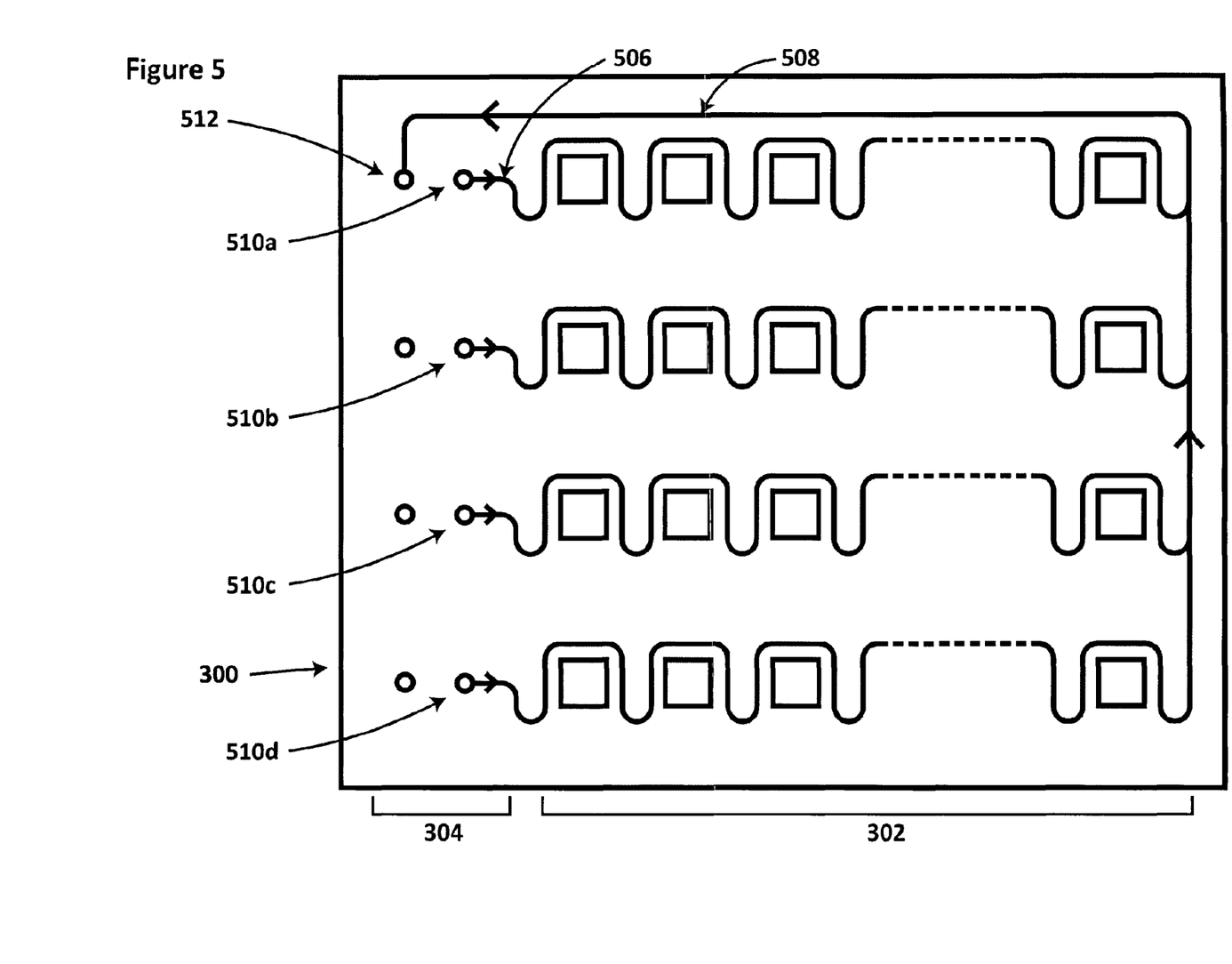
FIG. 5 illustrates further detail of the biological microfluidics chip of FIG. 3.

FIG. 5 illustrates ports and channels that are used to control the temperature within the wells 302 of the biochip 300. In this example, the wells 302 are square in cross-section when viewed from above, but other shapes are possible.

In this example, there are four temperature control inlet ports 510a, 510b, 510c, 510d, one for each row of the array of wells 302. In this way, the temperature of the wells 302 in each row can be independently controlled. The biochip 300 comprises a single temperature control outlet port 512. Other possible configurations include having a single inlet and a single outlet temperature control port, and in such embodiments the whole biochip can be maintained at a uniform temperature.

Extending from each of the temperature control inlet ports 510a, 510b, 510c, 510d, is a temperature control channel 506. The temperature control channel 506 can transport a temperature control liquid from the inlet port 510a, 510b, 510c, 510d to the outlet port 512 along a path that is in proximity to the wells 302 in the row that is associated with the temperature inlet port 510a, 510b, 510c, 510d. It will be appreciated that "in proximity" means that the temperature control channel 506 is located close enough to the wells 302 such that heat can be exchanged between the contents of the well 302 and the temperature control fluid in the temperature control channel 506. Heat may be exchanged either to or from the temperature control fluid in order to either cool or heat the contents of the well 302.

In this example, the temperature control channel 506 follows a path that is adjacent to three of the four sides of the horizontal square cross-section of the wells 302 in order to evenly heat or cool the contents of the wells. It will be appreciated that the temperature control channel 506 may take any path in relation to the wells 302 as long as heat can be exchanged between temperature control fluid in the temperature control channel 506 and the contents of the wells 302. In examples where the wells 302 have a circular horizontal cross-section, the temperature control channel 506 may follow some, or substantially all, of the circumference of the circular well.

The temperature control channels 506 for each of the rows of wells all join together after they have passed by the wells in order to form a common temperature control return channel 508 that is in fluid communication with the temperature control outlet port 512.

Prior art products are known to use external heating modules to maintain steady experimental temperatures for wells in a biochip. In the prior art systems, the microtiter plate must remain fixed on the heating module at all times, and this can make it impossible to relocate the plate during use. Therefore, prior art microtiter plates cannot be easily used in automated robotic handling systems for high-throughput screening if a uniform temperature is required per well. In contrast, embodiments of a biochip described herein can have built-in heating/cooling channels and, therefore, do not have to be fixed on a thermostatic module, but can be moved freely in robotic systems. This provides a more flexible, in terms of usage, biochip than microtiter plates of the prior art.

Embodiments described herein can be used to perform experiments on zebrafish embryos/larvae in the wells, and the development of the embryos/larvae over a period of days can be monitored, for example, with or without exposure to drugs or other compounds. In other embodiments, experiments can be performed on a monolayer of cells, on a membrane, matrix or other substratum within the well.

In this embodiment, the biochip uses glass and/or (fused) silica as base compound(s). This can reduce autofluorescence significantly when compared with known polystyrene products that are used for 96-well microtiter plates. Glass can be considered a less expensive material, whereas a combination of glass and polystyrene can be more expensive due to the coating technology required. Furthermore, glass can be more resistant to scratching and to repeated cleaning cycles, than plastics.

In this example, the surface of the biochip is glass, which enables imaging operations to refocus on a specimen within 0.1 seconds. In contrast, known biochips having a polystyrene surface generate drift due to a relatively rough surface of the biochip and deflection of infrared wavelengths that are used as part of an imaging operation. This can mean that refocusing for a prior art biochip can take more than 1 second per well, and this adds up logarithmically in time for large batch embryo screenings.

Figure 6:
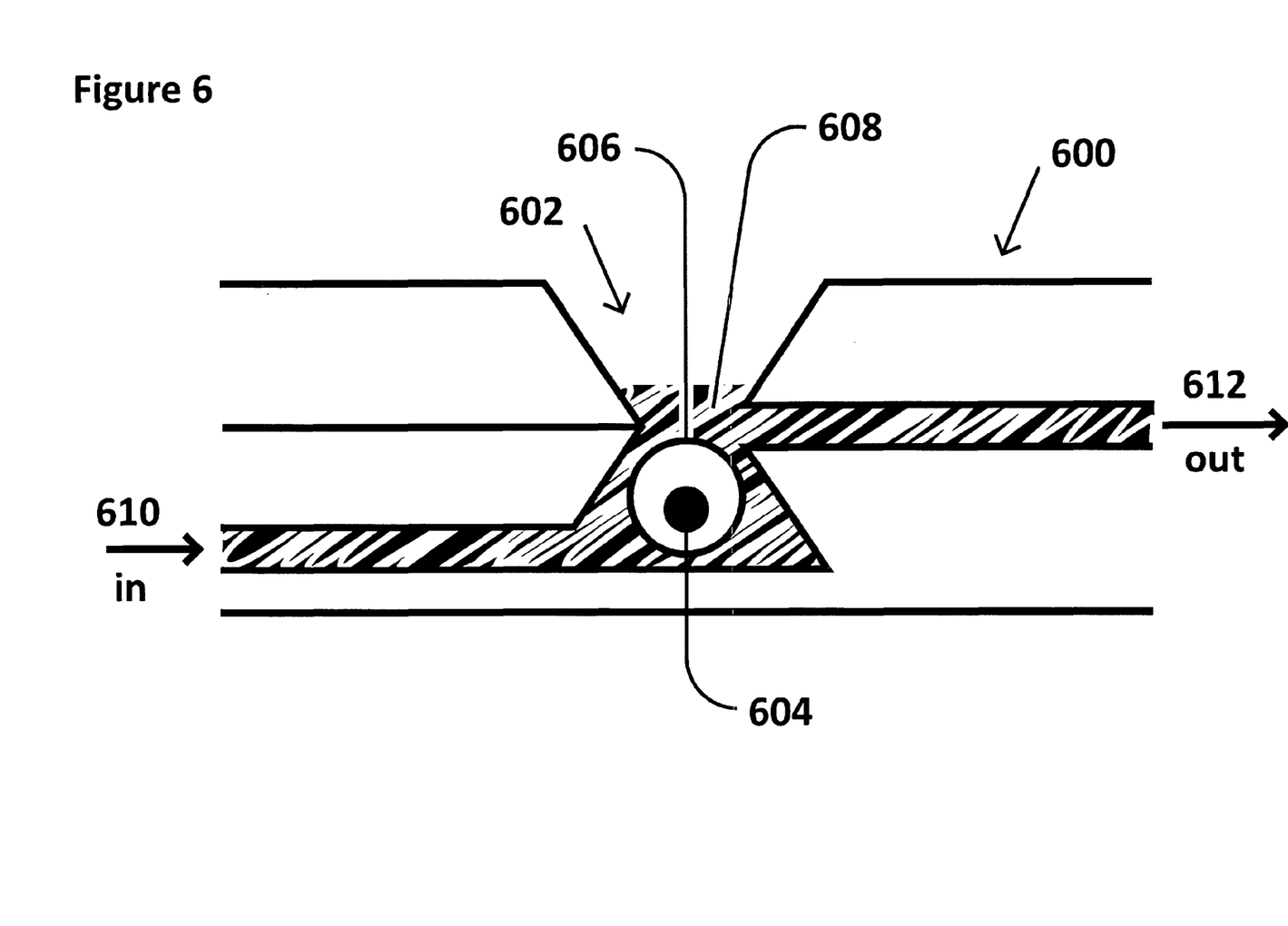
FIG. 6 illustrates a biological microfluidics chip according to an embodiment of this disclosure in use.

FIG. 6 illustrates a vertical cross-sectional view of a well 602 of a biochip 600 according to an embodiment of the disclosure described herein, in use, performing an experiment on a zebrafish embryo 604.

In this example, the embryo 604 is surrounded by its chorion 606 and embedded in low-melting point agarose 608 (injected into the well by a robotic handler) to prevent the embryo from moving around in the well. The agarose 608 solidifies into a gel but does not damage the specimen or prevent gas/nutrient exchange, and can be convenient for injecting test drugs through the extra-embryonic membrane (chorion 606). The gel 608 can also limit the spread of a potential infection. Each well 602 in the biochip 600 will have a steady or constant supply of defined buffer through its microfluidic inlet channels 610 that run in parallel, thereby reducing the risk of microbial cross-contamination and leakage of drug to neighboring wells. In addition, drugs can be administered by robotic pipette handlers through a sliding lid, which may be plastic or glass, and can be retracted to expose the opening in the well for injection. Alternatively, the lid may be a self-sealing lid, for example, a rubber or polymer plug, laminate film or adhesive tape. It should be appreciated that the presence of agarose 608 is not essential, and in other embodiments, the embryos can lie free in the fluid in the well or in any other substance.

Some embodiments of a biochip described herein can comprise a lid that is configured to cover the openings of the wells in the top surface of the biochip substrate. The lid may be a sliding lid that is integrated as part of the biochip. This can enable the lid to be slid to one side to an open position to expose the openings of the wells for embryos to be introduced prior to the start of the experiment, and/or to enable drugs to be introduced during the experiment. The lid can then be slid back into a covered position during the experiment.

In some examples, the lid can seal the well gas- and/or fluid-tight to enable efficient microfluidic flow in the well. The removable lid can also enable recovery of an embryo after the experiment, and further detailed analyses (for example, polymerase chain reaction (PCR), extraction of mRNA, etc.) can be performed after the end of the experiment in the biochip. Removal of the lid can also allow for convenient cleaning of the wells after the end of an experiment so that the biochip can be re-used.

In some embodiments, the lid can be heated so as to reduce the likelihood of condensation building up on the lid. A reduction in condensation can enable more accurate imaging operations to be performed through the lid in use. Alternatively, the lid may consist of a plastic film, applied under heat, or a perforated membrane whose perforations are aligned with the upper openings of the wells, and with a glass cover applied over the membrane. Where the lid is a film, it can be self-sealing after a needle has been passed through it into the well. In some cases, the lid is optically clear/transparent to permit microscopic analysis of the well contents; in other cases, it may have a mirrored upper or lower surface.

Figure 7:
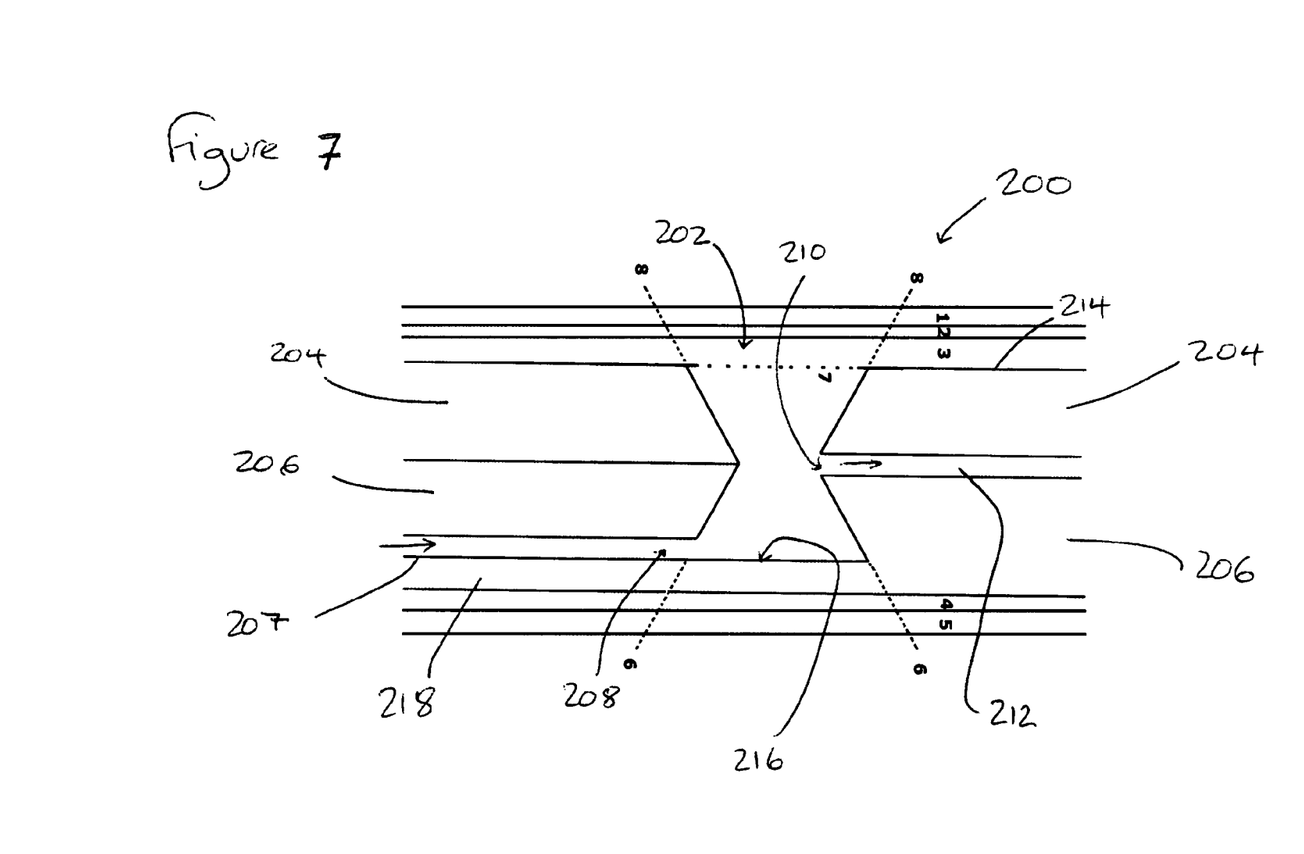
FIG. 7 illustrates a biological microfluidics chip in a holder according to the disclosure described herein.

FIG. 7 illustrates a vertical cross-sectional view of a well 202 of a biochip 200 according to an embodiment of the disclosure (as in FIG. 2), when placed in a holder according to the present disclosure. The holder comprises several layers of materials that, when connected, e.g., by screws, can fixate the biochip in a particular position. The top lid 1 is made of metal, plastic, or other material. The plate 2 is a glass plate or polymer seal, that can be mounted on top seal layer 3. Top seal layer 3 is, for example, made of silicone. Bottom seal layer 4 is also made of silicone. The bottom layer constitutes the bottom lid 5, which can be made of metal and/or plastic or other material. The angle between dotted lines 6 indicates the bottom side field of view for imaging. Dotted line 7 indicates the location of the hole in top seal layer 3 for imaging purposes. The angle between dotted lines 8 indicates the top side field of view for imaging. The holder of the present disclosure is not limited to this particular configuration.

Now described are specific implementation details of a biological microfluidics chip according to an embodiment of this disclosure. This embodiment of a biological microfluidics chip can be made from D263 glass, as this type of glass has been found to reduce autofluorescence compared to known polystyrene products.

The cross-sectional area of a well in the biochip is 2-4 mm$^2$. This is in contrast to known 96-well microtiter plates where the cross-sectional area of a well is significantly larger, namely 33.18 mm$^2$ (surface area ($\pi r^2$) r=3.25 mm; h=10 mm). Therefore, this embodiment of the biochip can reduce automated "find and mark" time when used in automated systems.

The volume of a single well in the biochip of this embodiment is 8 mm$^3$=8 µl (2 mm×2 mm×2 mm). This is in contrast to the well volume of known 96-well plates, which is typically around 250-331 mm$^3$ (33.18 mm$^2$*(7.5 mm or 10 mm)). Therefore, this embodiment of the biochip can provide a cost reduction in compound use, and is estimated to be a reduction of 31-41% (250/8 to 331/8).

In this example, the biochip is able to accommodate 869 wells in the same area that a conventional microtiter plate would hold 96 wells per plate. This is because the surface area of a 96-well plate (total area 7823 mm$^2$; width×depth; 72.3 mm×108.2 mm) is approximately 0.012 well/mm$^2$. By contrast, a biochip according to an embodiment of the disclosure, can accommodate ≥0.11 wells/mm$^2$ (surface area of each well, plus its associated microfluidic channels, is 3 mm×3 mm).

Embodiments described herein can be used to perform experiments in wells of a biological microfluidics chip. The subject of the experiment, such as an embryo, can be inserted into an upper opening in the substrate that defines the well. Optionally, the upper opening in the substrate can be covered with a lid as described above.

Examples described herein can immobilize an embryo or other subject in the well before subsequently exposing the subject to one or more fluids received from a microfluidic channel that opens into an opening in a wall of the well. As an example, the fluids may provide nutrients for the subject. The subject may not be moved to or from the well through a microfluidic channel.

The wells of one or more biological microfluidics chips described herein may be considered as a holding chamber for growth of a subject, and may be considered to relate to long-term culture experiments/systems. "Long-term" may be considered to be of the order of a few days, for example, five days.

Biological microfluidics chips may be considered to be in a different technical field to microfluidic worm-sorters, wherein a worm is captured in an enclosed chamber by suction. Different technical considerations may be necessary for such microfluidic sorters compared with biological microfluidics chips having wells as described herein.

The invention claimed is:

1. A biological microfluidics chip comprising:
   a substrate;
   a microfluidic inlet port defining an opening in a surface of the substrate;
   a microfluidic outlet port defining an opening in a surface of the substrate;
   a plurality of wells extending from a top surface of the substrate, wherein each well is bounded by one or more walls, and an inlet opening and an outlet opening are provided in a wall of each of the plurality of wells;
   one or more microfluidic inlet channels in the substrate that connect the microfluidic inlet port to each of the inlet openings in the walls of the wells, wherein the length of the channel between the main artery of the microfluidic inlet channel and the inlet opening in the wall of a well varies such that the entire length of a microfluidic channel between the microfluidic inlet port and an inlet opening in the wall of a well is substantially the same for every well of the plurality of wells within the substrate;
   one or more microfluidic inlet channels in the substrate that connect each of the outlet openings in the walls of the wells to the microfluidic outlet port;
   a temperature control inlet port and a temperature control outlet port; and
   a temperature control channel configured to transport temperature control fluid from the temperature control inlet port to the temperature control outlet port along a path that is in proximity to one or more of the plurality of wells such that, in use, heat is exchangeable between the temperature control liquid and the contents of the wells.

2. The biological microfluidics chip of claim 1, wherein one or more of the temperature control inlet port, temperature control outlet port and temperature control channels are provided for a subset of the plurality of wells.

3. The biological microfluidics chip of claim 2, wherein the plurality of wells comprises an array of wells, and a separate temperature control inlet port and temperature control channel are provided for each row of the array of wells.

4. The biological microfluidics chip of claim 1, wherein the location of the inlet opening in a wall of each of the wells is lower than the outlet opening.

5. The biological microfluidics chip of claim 1, further comprising:
   a second microfluidic inlet port; and
   a second inlet opening in the walls of the wells;
   wherein the second inlet opening is in fluid communication with the second microfluidic inlet port by a second microfluidic inlet channel.

6. The biological microfluidics chip of claim 5, wherein the second inlet opening in the wall of the wells is located lower than the outlet opening in the wall of the wells.

7. The biological microfluidics chip of claim 1, further comprising a lid.

8. The biological microfluidics chip of claim 1, wherein the substrate is, at least in part, D263 glass.

9. The biological microfluidics chip of claim 1, wherein the plurality of wells have a shape in vertical cross-section comprising two frustoconical shapes end to end to end, wherein the narrower ends of the frustoconical shapes are collocated.

10. The biological microfluidics chip of claim 9, wherein the substrate comprises a top and a bottom layer, and the two frustoconical shapes are collected at the boundary between the top and bottom layer.

11. The biological microfluidics chip of claim 10, wherein the first and/or second microfluidic channels are provided between the top and bottom layer of the substrate.

12. The biological microfluidics chip of claim 1, wherein one or more of the microfluidic channels comprises a microfluidic valve.

13. The biological microfluidics chip of claim 7, wherein the lid is sliding, self-sealing, removable, and/or heated.

14. A method of utilizing the biological microfluidics chip of claim 1, the method comprising:
    providing cells, embryos or larvae to one or more of the plurality of wells, wherein the cells, embryos or larvae are for use in an experiment;
    providing a fluid to the microfluidic inlet port such that the fluid enters the one or more wells;
    removing a fluid from the one or more wells via the microfluidic outlet port; and
    imaging the contents of the one or more wells in order to obtain results of the experiment in the one or more wells.

15. The method of claim 14, further comprising:
    developing the cells, embryos or larvae in the one or more of the plurality of wells; and
    expose the cells, embryos or larvae to drugs or other compounds.

16. The method of claim 14, in which the cells are stem cells.

17. The method of claim 14, in which the assay is used for human, animal, microorganism or plant studies or screens.

18. The method of claim 14, in which photosynthetic bodies are cultured within the plurality of wells.

19. The method of claim 14, further comprising providing a temperature control fluid to a temperature control inlet port of the biological microfluidics chip in order to control the temperature of the contents of the one or more wells.

20. A biological microfluidics chip comprising:
    a substrate;
    a microfluidic inlet port defining an opening in a surface of the substrate;
    a microfluidic outlet port defining an opening in a surface of the substrate;
    a plurality of wells extending from a top surface of the substrate, wherein each well is bounded by one or more walls, and an inlet opening and an outlet opening are provided in a wall of each of the plurality of wells;
    one or more microfluidic inlet channels in the substrate that connect the microfluidic inlet port to each of the inlet openings in the walls of the wells; and
    one or more microfluidic outlet channels in the substrate that connect each of the outlet openings in the walls of the wells to the microfluidic outlet port, wherein the length of the channel between the main artery of the microfluidic inlet channel and the inlet opening in the wall of a well varies such that the entire length of a microfluidic channel between the microfluidic inlet port and an inlet opening in the wall of a well is substantially the same for every well of the plurality of wells within the substrate.

* * * * *